US012562274B2

(12) United States Patent
Morris et al.

(10) Patent No.: US 12,562,274 B2
(45) Date of Patent: Feb. 24, 2026

(54) METHODS, SYSTEMS, AND COMPUTER PROGRAM PRODUCTS USING ARTIFICIAL INTELLIGENCE FOR COORDINATED IDENTIFICATION OF PATIENTS FOR A CLINICAL TRIAL THAT ARE SERVED BY MULTIPLE PROVIDERS

(71) Applicant: Change Healthcare Holdings LLC, Nashville, TN (US)

(72) Inventors: V. Scott Morris, Greenville, SC (US); Faisal Mushtaq, West Harrison, NY (US); Sanjoy Mondal, Sunnyvale, CA (US); Mark Fidow, San Ramon, CA (US)

(73) Assignee: Change Healthcare Holdings LLC, Nashville, TN (US)

( * ) Notice: Subject to any disclaimer, the term of this patent is extended or adjusted under 35 U.S.C. 154(b) by 235 days.

(21) Appl. No.: 17/218,487

(22) Filed: Mar. 31, 2021

(65) Prior Publication Data

US 2022/0319697 A1    Oct. 6, 2022

(51) Int. Cl.

| | |
|---|---|
| *G16H 50/20* | (2018.01) |
| *G06F 40/284* | (2020.01) |
| *G06N 3/04* | (2023.01) |
| *G06N 3/08* | (2023.01) |
| *G06Q 10/10* | (2023.01) |
| *G16H 10/20* | (2018.01) |
| *G16H 10/60* | (2018.01) |
| *G16H 40/20* | (2018.01) |
| *G16H 50/70* | (2018.01) |

(Continued)

(52) U.S. Cl.
CPC ........... *G16H 50/20* (2018.01); *G06F 40/284* (2020.01); *G06N 3/04* (2013.01); *G06N 3/08* (2013.01); *G06Q 10/10* (2013.01); *G16H 10/20* (2018.01); *G16H 10/60* (2018.01); *G16H 40/20* (2018.01); *G16H 50/70* (2018.01); *G16H 10/40* (2018.01); *G16H 70/20* (2018.01); *G16H 70/40* (2018.01); *G16H 70/60* (2018.01); *H04L 67/12* (2013.01)

(58) Field of Classification Search
CPC ...................................................... G16H 10/20
See application file for complete search history.

(56) References Cited

U.S. PATENT DOCUMENTS

| | | | |
|---|---|---|---|
| 11,189,364 B1 * | 11/2021 | Shaw | ..................... G06N 20/00 |
| 11,196,656 B1 | 12/2021 | Jain et al. | |

(Continued)

*Primary Examiner* — Devin C Hein
(74) *Attorney, Agent, or Firm* — MARSHALL, GERSTEIN & BORUN LLP

(57) ABSTRACT

A method includes receiving patient medical record information from each of a plurality of providers, the plurality of providers being associated with a plurality of different organizational managing entities, respectively; querying the patient medical record information of each of the plurality of providers using selection criteria to identify a first subset patients having first characteristics that match first screening requirements for a clinical trial; identifying, using an artificial intelligence engine, ones of the first subset of patients whose medical record information includes second characteristics that match second screening requirements for the clinical trial as clinical trial patient candidates; and communicating identities of the clinical trial patient candidates to ones of the plurality of providers that provide healthcare services to the clinical trial patient candidates, respectively.

13 Claims, 7 Drawing Sheets

(51) Int. Cl.

| | | |
|---|---|---|
| *G16H 70/20* | (2018.01) | |
| *G16H 10/40* | (2018.01) | |
| *G16H 70/40* | (2018.01) | |
| *G16H 70/60* | (2018.01) | |
| *H04L 67/12* | (2022.01) | |

(56) References Cited

U.S. PATENT DOCUMENTS

| | | | | |
|---|---|---|---|---|
| 11,328,796 | B1 * | 5/2022 | Jain | G16H 10/20 |
| 2002/0002474 | A1 * | 1/2002 | Michelson | G16H 10/60 |
| | | | | 705/3 |
| 2008/0010254 | A1 * | 1/2008 | Settimi | G06Q 10/06 |
| 2010/0088245 | A1 * | 4/2010 | Harrison | G06Q 10/10 |
| | | | | 705/317 |
| 2012/0316898 | A1 * | 12/2012 | Levitt | G16H 10/20 |
| | | | | 705/3 |
| 2013/0304504 | A1 * | 11/2013 | Powell | G06Q 10/06 |
| | | | | 705/3 |
| 2015/0058627 | A1 * | 2/2015 | Paffel | G16H 10/60 |
| | | | | 713/168 |
| 2017/0039325 | A1 * | 2/2017 | Dorsett | H04L 51/02 |
| 2019/0095805 | A1 * | 3/2019 | Tristan | G06N 5/045 |
| 2020/0020423 | A1 * | 1/2020 | Wu | G16H 50/70 |
| 2020/0176098 | A1 * | 6/2020 | Lucas | G16H 10/60 |
| 2022/0084633 | A1 * | 3/2022 | Das | G16H 50/20 |
| 2022/0208313 | A1 * | 6/2022 | Jones | G06Q 10/0631 |
| 2022/0208376 | A1 * | 6/2022 | Sutton | G16H 50/20 |

* cited by examiner

100

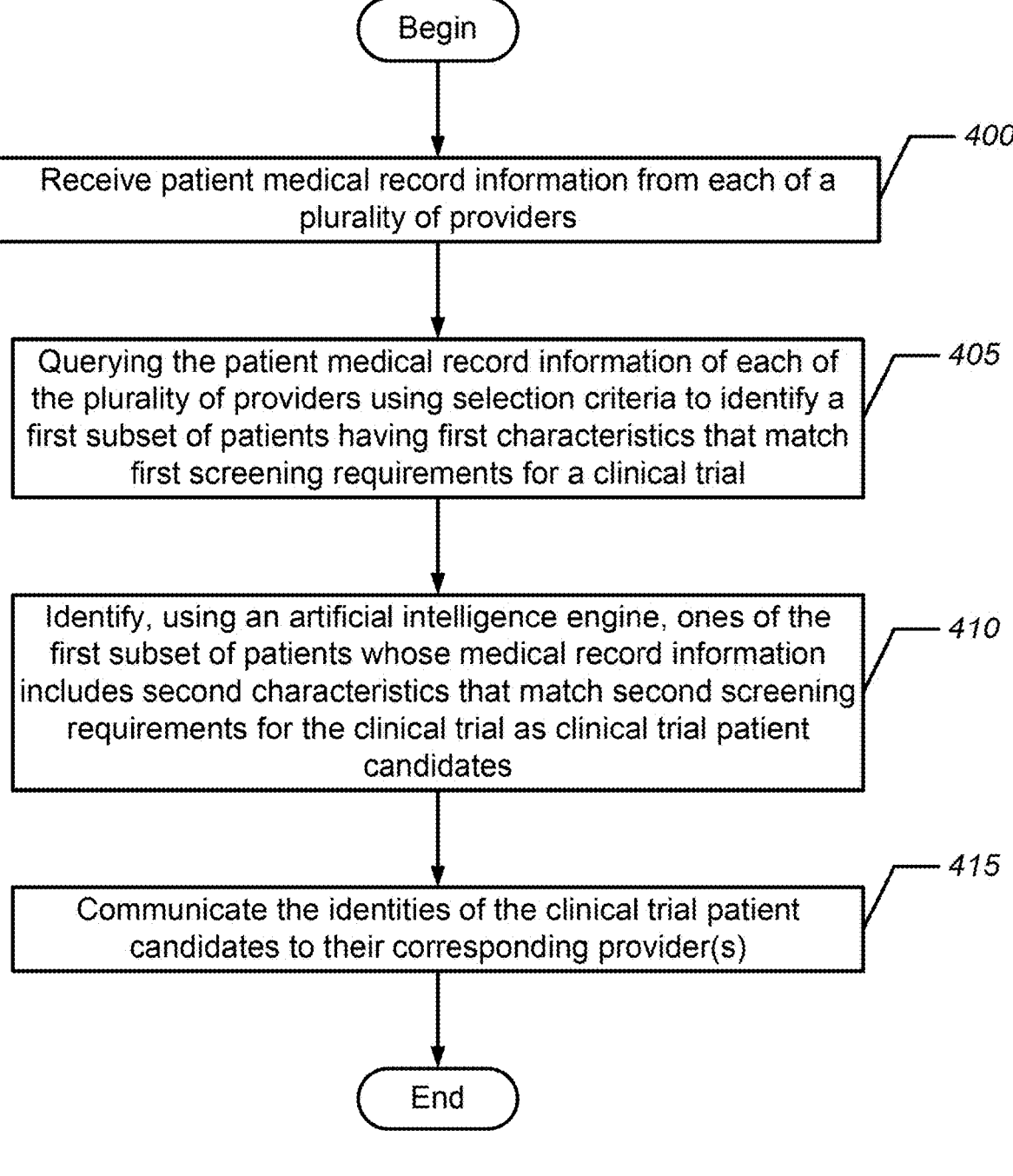

Begin

Receive patient medical record information from each of a plurality of providers — 400

Querying the patient medical record information of each of the plurality of providers using selection criteria to identify a first subset of patients having first characteristics that match first screening requirements for a clinical trial — 405

Identify, using an artificial intelligence engine, ones of the first subset of patients whose medical record information includes second characteristics that match second screening requirements for the clinical trial as clinical trial patient candidates — 410

Communicate the identities of the clinical trial patient candidates to their corresponding provider(s) — 415

End

METHODS, SYSTEMS, AND COMPUTER PROGRAM PRODUCTS USING ARTIFICIAL INTELLIGENCE FOR COORDINATED IDENTIFICATION OF PATIENTS FOR A CLINICAL TRIAL THAT ARE SERVED BY MULTIPLE PROVIDERS

FIELD

The present inventive concepts relate generally to health care systems and services and, more particularly, identification and recruitment of patients for clinical trials.

BACKGROUND

Many clinical trials are behind schedule due to enrollment delays and lack of awareness of patients about the opportunity to access alternative treatment options through clinical research. The delays in conducting clinical trials may cause delays in the testing and approval of new therapies for those who need them. Statistics have shown that less than 1% of patients participate in clinical trials. Due to the small number of participants, clinical trials may have significant enrollment challenges to ensure there is an appropriate diversity of participants. Oftentimes a large majority of potentially eligible patients are seen in a community care center where research is not taking place and patients' medical records are not screened. In provider facilities where clinical research is conducted, as little as 5% of patient records may be screened. Lack of awareness of ongoing trials by treating physicians caused by the lack of a defined role for physicians in the trial recruitment process further limits patient enrollment into clinical trials

SUMMARY

According to some embodiments of the inventive concept, a method comprises receiving patient medical record information from each of a plurality of providers, the plurality of providers being associated with a plurality of different organizational managing entities, respectively; querying the patient medical record information of each of the plurality of providers using selection criteria to identify a first subset of patients having first characteristics that match first screening requirements for a clinical trial; identifying, using an artificial intelligence engine, ones of the first subset of patients whose medical record information includes second characteristics that match second screening requirements for the clinical trial as clinical trial patient candidates; and communicating identities of the clinical trial patient candidates to ones of the plurality of providers that provide healthcare services to the clinical trial patient candidates, respectively.

In other embodiments, the first screening requirements define individual thresholds for one or more of the selection criteria and a matching threshold for a number of the individual thresholds that must be met to match.

In still other embodiments, the selection criteria comprise demographic information, one or more diagnosis codes, laboratory test values, medication names, scores for cognitive tests, medical professional observations, acute condition names, chronic condition names, and/or allergy names.

In still other embodiments, the plurality of providers is a first plurality of providers, the method further comprising: receiving patient claim information associated with a second plurality of providers, a number of the second plurality of providers being greater than a number of the first plurality of providers; and querying the patient claim information of each of the second plurality of providers using demographic information, one or more diagnosis codes, and/or pharmacy information to identify the first plurality of providers having patients with third characteristics that match third screening requirements for the clinical trial.

In still other embodiments, the method further comprises receiving a communication from each of the first plurality of providers opting in to participating in the clinical trial.

In still other embodiments, the method further comprises discarding ones of the first plurality of providers having a number of patients with the third characteristics that match the third screening requirements that does not exceed a threshold.

In still other embodiments, the method further comprises identifying the first plurality of providers based on geographic information for the first plurality of providers obtained from the patient claim information.

In still other embodiments, the second screening requirements comprise clinical characteristics associated with subject matter of the clinical trial. Identifying, using the artificial intelligence engine, ones of the first subset of patients whose medical record information includes second characteristics that match second screening requirements for the clinical trial as clinical trial patient candidates comprises: determining, using a machine learning engine or a multi-layer neural network, whether medical record chart data for the first subset of patients matches any of the clinical characteristics associated with the subject matter of the clinical trial; and determining, using a content similarity engine, whether free-text written by a health care practitioner contained in the medical record chart data for the first subset of patients matches any of the clinical characteristics associated with the subject matter of the clinical trial.

In still other embodiments, the second screening requirements define individual thresholds for one or more of the second characteristics and a matching threshold for a number of the individual thresholds that must be met to match.

In still other embodiments, communicating identities of the clinical trial patient candidates to ones of the plurality of providers that provide healthcare services to the clinical trial patient candidates, respectively, comprises: providing access to the identities of ones of the clinical trial patient candidates receiving healthcare services from one of the plurality of providers via a networked results portal accessible by the one of the plurality of providers.

In still other embodiments, communicating identities of the clinical trial patient candidates to ones of the plurality of providers that provide healthcare services to the clinical trial patient candidates, respectively, comprises: asynchronously transmitting a communication containing the identities of ones of the clinical trial patient candidates receiving healthcare services from one of the plurality of providers to the one of the plurality of providers.

In some embodiments of the inventive concept, a system comprises a processor; and a memory coupled to the processor and comprising computer readable program code embodied in the memory that is executable by the processor to perform operations comprising: receiving patient medical record information from each of a plurality of providers, the plurality of providers being associated with a plurality of different organizational managing entities, respectively; querying the patient medical record information of each of the plurality of providers using selection criteria to identify a first subset patients having first characteristics that match first screening requirements for a clinical trial; identifying, using an artificial intelligence engine, ones of the first subset of patients whose medical record information includes second characteristics that match second screening requirements for the clinical trial as clinical trial patient candidates; and communicating identities of the clinical trial patient candidates to ones of the plurality of providers that provide healthcare services to the clinical trial patient candidates, respectively.

In further embodiments, the plurality of providers is a first plurality of providers, the operations further comprising: receiving patient claim information associated with a second plurality of providers, a number of the second plurality of providers being greater than a number of the first plurality of providers; and querying the patient claim information of each of the second plurality of providers using demographic information, one or more diagnosis codes, and/or pharmacy information to identify the first plurality of providers having patients with third characteristics that match third screening requirements for the clinical trial.

In still further embodiments, the operations further comprise: receiving a communication from each of the first plurality of providers opting in to participating in the clinical trial.

In still further embodiments, the second screening requirements comprise clinical characteristics associated with subject matter of the clinical trial. Identifying, using the artificial intelligence engine, ones of the first subset of patients whose medical record information includes second characteristics that match second screening requirements for the clinical trial as clinical trial patient candidates comprises: determining, using a machine learning engine or a multi-layer neural network, whether medical record chart data for the first subset of patients matches any of the clinical characteristics associated with the subject matter of the clinical trial; and determining, using a content similarity engine, whether free-text written by a health care practitioner contained in the medical record chart data for the first subset of patients matches any of the clinical characteristics associated with the subject matter of the clinical trial.

In still further embodiments, communicating identities of the clinical trial patient candidates to ones of the plurality of providers that provide healthcare services to the clinical trial patient candidates, respectively, comprises: providing access to the identities of ones of the clinical trial patient candidates receiving healthcare services from one of the plurality of providers via a networked results portal accessible by the one of the plurality of providers; or asynchronously transmitting a communication containing the identities of ones of the clinical trial patient candidates receiving healthcare services from the one of the plurality of providers to the one of the plurality of providers.

In some embodiments of the inventive concept, a computer program product, comprises a non-transitory computer readable storage medium comprising computer readable program code embodied in the medium that is executable by a processor to perform operations comprising: receiving patient medical record information from each of a plurality of providers, the plurality of providers being associated with a plurality of different organizational managing entities, respectively; querying the patient medical record information of each of the plurality of providers using selection criteria to identify a first subset patients having first characteristics that match first screening requirements for a clinical trial; identifying, using an artificial intelligence engine, ones of the first subset of patients whose medical record information includes second characteristics that match second screening requirements for the clinical trial as clinical trial patient candidates; and communicating identities of the clinical trial patient candidates to ones of the plurality of providers that provide healthcare services to the clinical trial patient candidates, respectively.

In other embodiments, the plurality of providers is a first plurality of providers, the operations further comprising: receiving patient claim information associated with a second plurality of providers, a number of the second plurality of providers being greater than a number of the first plurality of providers; querying the patient claim information of each of the second plurality of providers using demographic information, one or more diagnosis codes, and/or pharmacy information to identify the first plurality of providers having patients with third characteristics that match third screening requirements for the clinical trial; and receiving a communication from each of the first plurality of providers opting in to participating in the clinical trial.

In still other embodiments, the second screening requirements comprise clinical characteristics associated with subject matter of the clinical trial. Identifying, using the artificial intelligence engine, ones of the first subset of patients whose medical record information includes second characteristics that match second screening requirements for the clinical trial as clinical trial patient candidates comprises: determining, using a machine learning engine or a multilayer neural network, whether medical record chart data for the first subset of patients matches any of the clinical characteristics associated with the subject matter of the clinical trial; and determining, using a content similarity engine, whether free-text written by a health care practitioner contained in the medical record chart data for the first subset of patients matches any of the clinical characteristics associated with the subject matter of the clinical trial.

In still other embodiments, communicating identities of the clinical trial patient candidates to ones of the plurality of providers that provide healthcare services to the clinical trial patient candidates, respectively, comprises: providing access to the identities of ones of the clinical trial patient candidates receiving healthcare services from one of the plurality of providers via a networked results portal accessible by the one of the plurality of providers; or asynchronously transmitting a communication containing the identities of ones of the clinical trial patient candidates receiving healthcare services from the one of the plurality of providers to the one of the plurality of providers.

It is noted that aspects described with respect to one embodiment may be incorporated in different embodiments although not specifically described relative thereto. That is, all embodiments and/or features of any embodiments can be combined in any way and/or combination. Moreover, other methods, systems, articles of manufacture, and/or computer program products according to embodiments of the inventive concept will be or become apparent to one with skill in the art upon review of the following drawings and detailed description. It is intended that all such additional systems, methods, articles of manufacture, and/or computer program products be included within this description, be within the scope of the present inventive subject matter and be protected by the accompanying claims. It is further intended that all embodiments disclosed herein can be implemented separately or combined in any way and/or combination.

BRIEF DESCRIPTION OF THE DRAWINGS

Other features of embodiments will be more readily understood from the following detailed description of specific embodiments thereof when read in conjunction with the accompanying drawings, in which:

FIGS. 4-6 are flowcharts that illustrate operations for coordinated identification of patients served by multiple providers using the AI assisted clinical trial recruitment system of FIG. 1 in accordance with some embodiments of the inventive concept;

DETAILED DESCRIPTION

Figure 1:
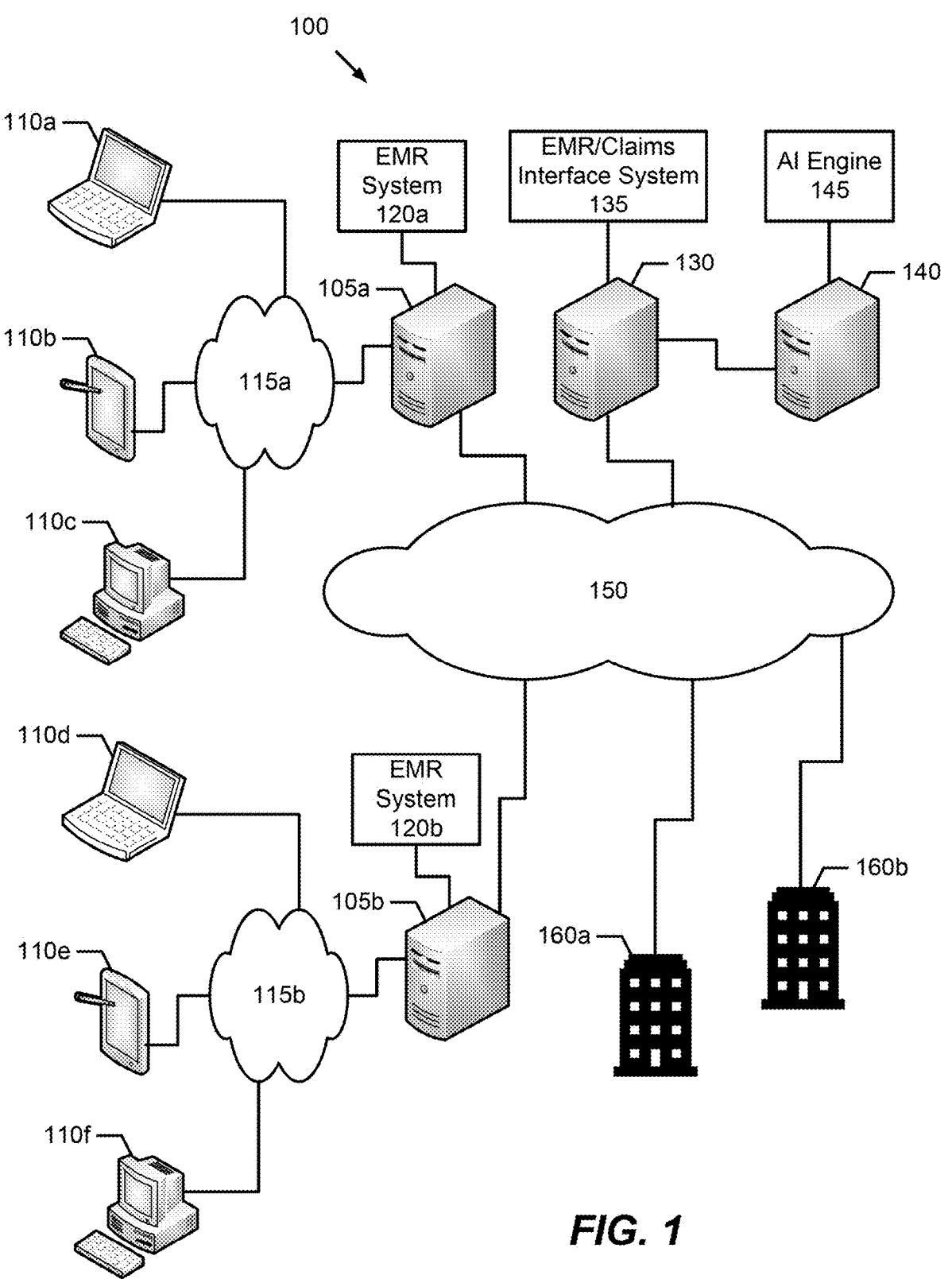
FIG. 1 is a block diagram that illustrates a communication network including an Artificial Intelligence (AI) assisted clinical trial recruitment system for coordinated identification of patients served by multiple providers in accordance with some embodiments of the inventive concept.

In the following detailed description, numerous specific details are set forth to provide a thorough understanding of embodiments of the present inventive concept. However, it will be understood by those skilled in the art that the present invention may be practiced without these specific details. In some instances, well-known methods, procedures, components and circuits have not been described in detail so as not to obscure the present inventive concept. It is intended that all embodiments disclosed herein can be implemented separately or combined in any way and/or combination. Aspects described with respect to one embodiment may be incorporated in different embodiments although not specifically described relative thereto. That is, all embodiments and/or features of any embodiments can be combined in any way and/or combination.

Embodiments of the inventive concept are described herein in the context of an artificial intelligence engine comprising a multi-layer neural network, a content similarity engine, which includes a natural language processor, and/or a machine learning system. It will be understood that other types of artificial intelligence systems can be used in other embodiments of the artificial intelligence engine including, but not limited to deep learning systems, and/or computer vision systems. Moreover, it will be understood that the multi-layer neural network described herein is a multi-layer artificial neural network comprising artificial neurons or nodes and does not include a biological neural network comprising real biological neurons.

Some embodiments of the inventive concept stem from a realization that a major factor delaying many clinical trials is the inability to recruit and enroll a sufficient number of patients as participants. Various approaches have been taken to encourage patients to enroll in trials, which typically involve analyzing anonymous patient data to determine locations, e.g., geographic locations containing provider facilities that appear to serve many of the type of patient sought for a particular clinical trial and then attempting to reach these patients and encourage them to enroll in the trial.

This often involves social media campaigns, targeted mailings, advertisements, and the like aimed at potential enrollees. Such approaches rely on patients to contact their health care providers (e.g., physician or other professional) to request that they be evaluated for participation in a trial. Thus, to enroll a patient in a trial, they must be successfully notified of the existence of the trial through an outreach campaign that convinces the patient to contact their health care provider to request participation in the trial. Then, the health care provider must determine that the patient is indeed qualified and recommend the patient as a candidate for the trial. Due to the reliance on patients taking the initiative to drive their enrollment into a clinical trial, it is difficult to recruit patients in sufficient numbers to staff many trials.

Some embodiments of the inventive concept may provide an Artificial Intelligence (AI) assisted clinical trial recruitment system in which patient medical record information from multiple health care providers associated with different organizational management entities, i.e., the health care providers do not share any common management, is received. This medical record information is queried using selection criteria to identify a first subset of patients that have first characteristics that match first screening requirements for a clinical trial. A match determination may be made based on a threshold analysis for individual ones of the selection criteria and the number of thresholds that must be met in total to constitute a match. In some embodiments, the selection criteria may comprise demographic information, one or more diagnosis codes, and/or medical history information. For example, these selection criteria may include, but are not limited to, laboratory test values, medication names, scores for cognitive tests, medical professional observations, acute condition names, chronic condition names, and/or allergy names. An artificial intelligence engine may be used to identify those patients within the first subset of patients whose medical information includes second characteristics that match second screening requirements for the clinical trial. A match determination may be made on selected medical information including free-text generated by a health care practitioner in serving the patient. Similar to the first match determination, the second match determination may be made based on a threshold analysis for individual ones of the second screening requirements and the number of thresholds that must be met in total to constitute a match. Those patients that are determined to be matched based on the second screening requirements for the clinical trial may be identified as clinical trial patient candidates. The identities of these clinical trial patient candidates may then be communicated to the various providers that provide healthcare services to the patients to encourage these providers to make their own determination whether their patients would benefit by participating in the clinical trial and then consulting with these patients about enrolling in the trial. The identities of the clinical trial patient candidates may be communicated to the providers asynchronously by transmitting communications to the providers. In other embodiments, if the provider, for example, has an onsite trial coordinator, then the identities of the trial patient candidates may be communicated through a networked results portal for the trial that the provider has access to.

In some embodiments, the plurality of providers may be initially identified through review of patient claim information associated with the providers and querying the claim information using, for example, de-identified patient information, such as demographic information, one or more diagnosis codes, and/or pharmacy information. The providers may be selected using a threshold analysis to ensure that the number of trial patient candidates associated with the providers is greater than some lower bound based on the selection criteria used in the query. For example, some clinical trials may require a large number of participants and/or be associated with conditions that are prevalent in society, which may justify excluding some providers that may serve a low number of patients that may be candidates for such trials. Other clinical trials, however, may be associated with rare conditions such that providers serving a small number of potential patient candidates may nevertheless still be included among the selected providers. In some embodiments, providers may be geo-targeted using zip-codes or other geographic identifying indicia to select providers in a particular geographic area.

Once a provider has been identified as providing health care services to patients that may be potential clinical trial candidates, the provider may opt in to participating in the clinical trial allowing access to the provider's patients' medical record information. This relationship may carry forward for multiple trials, but the medical record information reviewed and processed is discarded and not used in determining patient candidacy for subsequent trials.

Referring to FIG. 1, a communication network 100 including an AI assisted clinical trial recruitment system for coordinated identification of patients served by multiple providers, in accordance with some embodiments of the inventive concept, comprises multiple health care provider facilities or practices. Each health care provider facility or practice may represent various types of organizations that are used to deliver health care services to patients via health care professionals, which are referred to generally herein as "providers." The providers may include, but are not limited to, hospitals, medical practices, mobile patient care facilities, diagnostic centers, lab centers, and the like. The providers may operate by providing health care services for patients and then invoicing one or more payors 160a and 160b for the services rendered. The payors 160a and 160b may include, but are not limited to, private insurance plans, government insurance plans (e.g., Medicare, Medicaid, state or federal public employee insurance plans), hybrid insurance plans (e.g., Affordable Care Act plans), private medical cost sharing plans, and the patients themselves. Two providers are illustrated in FIG. 1 with the first provider including a first health care facility server 105a coupled to devices 110a, 110b, and 110c via a network 115a. The health care facility server 105a may be configured with an Electronic Medical Record (EMR) system module 120a to manage patient files and facilitate the entry of orders for patients via health care service practitioners or personnel. Although shown as one combined system in FIG. 1, it will be understood that some health care facilities use separate systems for electronic medical record management and order entry management. The providers may use devices, such as devices 110a, 110b, and 110c to manage patients' electronic records and to issue orders for the patients through the EMR system 120a. An order may include, but is not limited to, a treatment, a procedure (e.g., surgical procedure, physical therapy procedure, radiologic/imaging procedure, etc.) a test, a prescription, and the like. The network 115a communicatively couples the devices 110a, 110b, and 110c to the health care facility server 105a. The network 115a may comprise one or more local or wireless networks to communicate with the health care facility server 105a when the health care facility server 105a is located in or proximate to the health care facility. When the health care facility server 105a is in a remote location from the health care facility, such as part of a cloud computing system or at a central computing center, then the network 115a may include one or more wide area or global networks, such as the Internet. The second provider is similar to the first provider and includes a second health care facility server 105b, which is configured with an EMR system module 120b. Devices 110d, 110e, and 110f are coupled to the second health care facility server 105b via a network 115b. In accordance with some embodiments of the inventive concept, the providers are associated with different organizational management entities, i.e., the health care providers do not share any common management.

According to embodiments of the inventive concept, clinical trial coordinators may use an AI assisted clinical trial recruitment system to coordinate identification of patients serviced by the multiple providers. The AI assisted clinical trial recruitment system may include a health care facility/payor interface server 130, which includes an EMR/claims interface system module 135 to facilitate the transfer of information between the EMR system 120, which the providers use to manage patient records and issue orders, and an AI server 140, which includes an AI engine module 145. The health care facility/payor interface server 130 and EMR/claims interface system module 135 are further configured to facilitate the transfer of claims information for various providers from the payors 160a and 160b to the AI server 140 and AI engine module 145. The AI server 140 and AI engine module 145 may be configured to receive patient information, provider information, order information, patient diagnoses, lab results, and other patient data contained in records in the EMR system 120 from the health care facility server 105 and EMR system module 120 by way of the health care facility interface server 130 and EMR/claims interface system module 135. The AI server 140 and AI engine module 145 may be further configured to receive claim information from the payors 160a and 160b by way of the health care facility interface server 130 and EMR/claims interface system module 135. The AI server 140 and AI engine module 145 may be configured to target individual patients of providers associated with different organizational management entities through querying the medical records of the providers to determine whether the patients satisfy various screening criteria for the clinical trial. The records may be queried through an iterative process with various thresholds set to determine whether the characteristics of the patient's medical records satisfy the trial screening criteria. In some embodiments, the providers may be identified using selection criteria applied to the claim data obtained from the payors 160a and 160b and associated with the providers. Once identified, the providers may choose to opt in to participate in patient recruitment for a current trial as well as future trials by providing access to patient medical records each time for each trial recruitment effort. The AI server 140 and AI engine module 145 may be configured communicate the results of the medical record analysis to the various providers having patients that have been identified as candidates for the clinical trial. The providers may then schedule consults with their patients to discuss the option of participating in the trial, which benefits the provider practice through additional consult fees as well as improves patient care by providing additional treatment or therapy options.

A network 150 couples the health care facility servers 105a and 105b to the health care facility/payor interface server 130 and couples the payors 160a and 160b to the health care facility/payor interface server 130. The network 150 may be a global network, such as the Internet or other publicly accessible network. Various elements of the network 150 may be interconnected by a wide area network, a local area network, an Intranet, and/or other private network, which may not be accessible by the general public. Thus, the communication network 150 may represent a combination of public and private networks or a virtual private network (VPN). The network 150 may be a wireless network, a wireline network, or may be a combination of both wireless and wireline networks.

The service provided through the health care facility interface server 130, EMR/claims interface system module 135, AI server 140, and AI engine module 145 to provide AI assisted coordinated identification of patients served by multiple providers for clinical trial recruitment may, in some embodiments, be embodied as a cloud service. For example, clinical trial coordinators may access the AI assisted clinical trial recruitment service as a Web service. In some embodiments, the AI assisted clinical trial recruitment service may be implemented as a Representational State Transfer Web Service (RESTful Web service).

Although FIG. 1 illustrates an example communication network including an AI assisted clinical trail recruitment system for coordinated identification of patients served by multiple providers, it will be understood that embodiments of the inventive subject matter are not limited to such configurations, but are intended to encompass any configuration capable of carrying out the operations described herein.

The AI engine 145 may be embodied in a variety of ways including, for example, but not limited to a multi-layer neural network, a natural language processing system, and a machine learning system.

Figure 2:
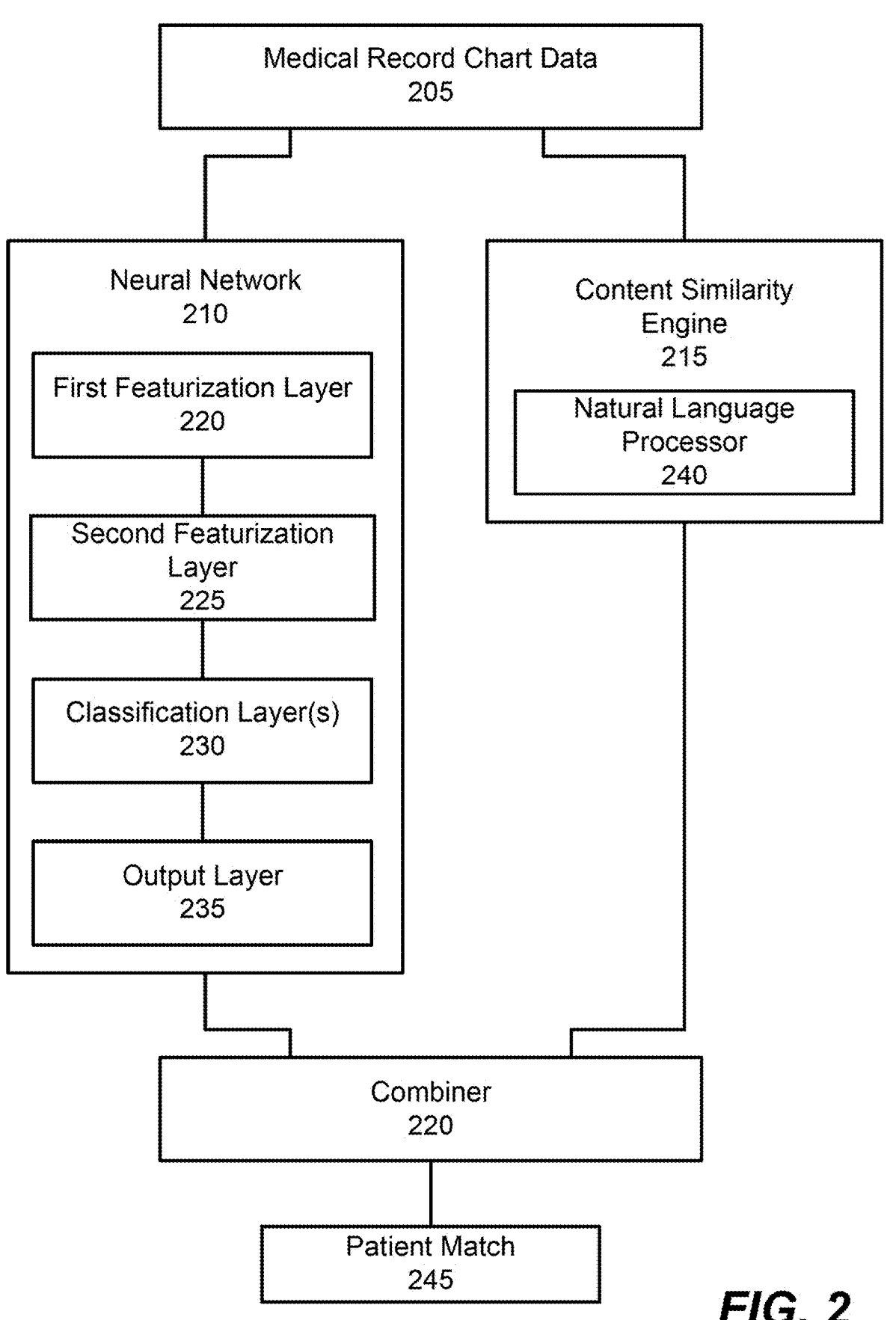
FIG. 2 is a block diagram of an AI engine incorporating a multi-layer neural network used in the AI assisted clinical trial recruitment system of FIG. 1 in accordance with some embodiments of the inventive concept.

FIG. 2 is a block diagram of the AI engine 145 used in the AI assisted clinical trial recruitment system in accordance with some embodiments of the inventive concept. As shown in FIG. 2, the AI engine 145 may include a medical record chart data module 205, a multi-layer neural network 210, a content similarity engine 215, and a combiner 220 that are connected as shown. The medical record chart data module 205 may be configured to receive information associated with a patient, information associated with a provider, information associated with an order for the patient, and any other information included in a patient's medical record including lab results, radiology images, physician or other health care practitioner free-text notes, etc. from, for example, a health care provider facility by way of the health care facility interface server 130 and EMR/claims interface system module 135. The patient information may include, but is not limited to, age, gender, problem list (e.g., description of one or more ailments or conditions the patient is suffering from), encounter diagnosis (the issue that causes a patient to visit the health care provider), patient class (e.g., in-patient or out-patient), and/or a medical center department (e.g., emergency room, cardiology, radiology, etc.). Note that a patient's encounter diagnosis may be different than a patient's problem list. For example, a patient may fall and receive a head injury, which may result in an encounter diagnosis of head trauma. The patient may nevertheless have a problem list description that includes heart disease and arthritis. The provider information may include, but is not limited to, a provider identifier and/or a provider specialty (e.g., cardiology, oncology, etc.). The order information may include, but is not limited to, an order name, order identification, order modality, order contrast, body area identification and/or a free-text reason for the order.

The medical record chart data module 205 may be configured to organize all of this information with the exception of the free-text reason for the order(s) or any free-text notes written into the patient's record by one or more health care practitioners into an input data set for the neural network 210.

The medical record chart data module 205 may be further configured to process any free-text input that may have been entered by a provider to generate a clinical input text for the content similarity engine 215. In some embodiments, the free-text reason input entered by the provider may be combined with additional information, such as a patient's encounter diagnosis and/or identification of an affected body area, to create the clinical input text that may capture clinical aspects of the reason for an order. The body area information may be obtained from the order that is being placed. For example, a computed tomography (CT) head exam indicates that the affected body area is the patient's head.

The neural network 210 may comprise multiple layers including a first featurization layer 220, a second featurization layer 225, one or more classification layer(s) 230, and an output layer 235. The first and second featurization layers 220 and 225 may be configured to automatically perform feature extraction on the input data set from the medical record chart data module 205 to reduce the dimensionality thereof so as to allow the neural network 210 to learn an efficient representation of the input data. According to some embodiments, the first featurization layer may be configured to numerically encode the categorical value information to create a categorical value information vocabulary, to embed the numerically encoded categorical value information into a categorical value information input vector, to numerically encode the sequence of categorical values information to create a sequence of categorical values vocabulary, and to embed the numerically encoded sequence of categorical values information into a sequence of categorical values information input vector. The encoding and embedding processes may comprise representing discrete numbers by a vector of continuous values representing a meaningful aspect of the input data set. The second featurization layer 225 may be configured to concatenate the scaled numerical value information output from the medical record chart data module 205 with the categorical value information input vector, and the sequence of categorical values information input vector. This concatenation may be viewed as a full representation of the input data set. One or more classification layer(s) 230 may be configured to perform supervised learning of correlations between the input data set, as represented by the vector and scaled numerical value information concatenation output from the second featurization layer 225, and clinical trial selection criteria or screening requirements.

The content similarity engine 215 may be configured to receive the clinical input text including free-text generated by one or more health care practitioners. A natural language processor module 240 may be configured to tokenize both the clinical input text and the clinical trial selection criteria or screening requirements into sequences of words to create a clinical input vocabulary and a clinical trial criteria/screening vocabulary, respectively. As part of this process, spelling errors may be corrected, synonyms may be resolved, and a maximum sequence length may be defined. Words may be weighted by how important they are based on their presence in the individual segment of text as well as in the full data set using, for example, a process called term frequency-inverse document frequency (td-idf) weighting. This may reduce the impact of common words used throughout the data set and may increase the impact of words specific to a segment of text. The natural language processor 240 may generate an encoded and embedded clinical input vector from the clinical input text and may generate a plurality of encoded and embedded clinical trial selection criteria/screening requirement vectors. The dot-product of the clinical input vector with each of the plurality of clinical trial selection criteria/screening requirement vectors may be used as a measure of similarity of the original free-text reason input with each of the clinical trial selection criteria/ screening requirements. If there are no words in common, then the dot-product would be zero. If the match is perfect, then the dot-product would be one. These dot-product values may be used as match scores for the clinical trial selection criteria/screening requirements.

The combiner 220 may receive the correlations between the input data set and clinical trial selection criteria or screening requirements output from the output layer 235 along with the match scores output by the content similarity engine 215. The combiner 220 may merge this information to evaluate whether particular elements of a patient's medical record data match various clinical trial selection criteria and screening requirements to satisfy defined thresholds for each individual clinical trial criterion or screening requirement and by the number of thresholds satisfied.

A determination may then be made whether there is a patient match at block 245 based on the threshold analysis performed with respect to the patient medical record data and the clinical trial selection criteria and screening requirements.

Figure 3:
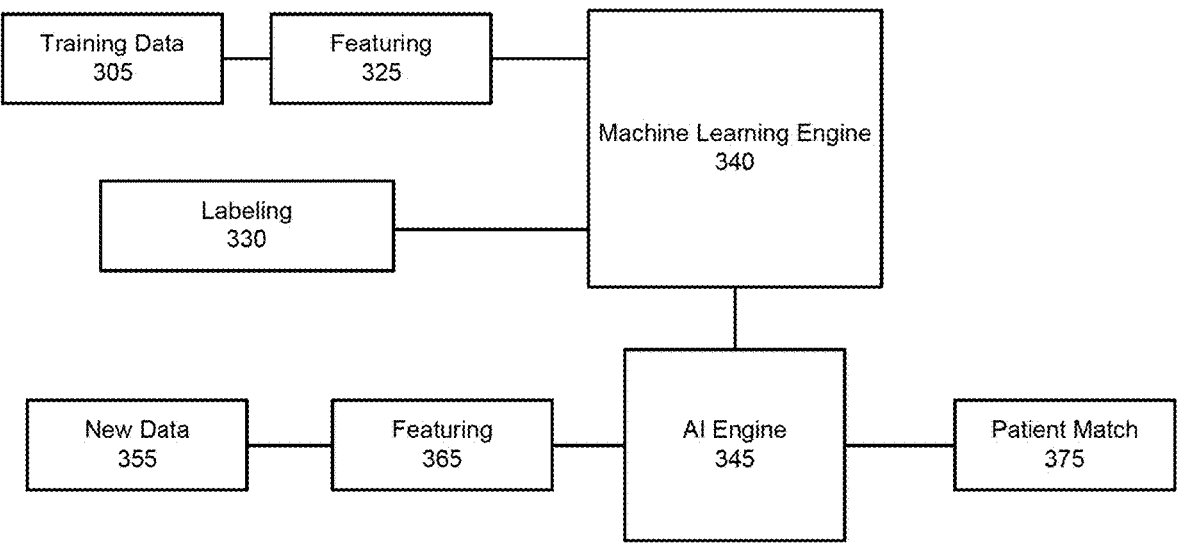
FIG. 3 is a block diagram of an AI engine incorporating a machine learning system used in the AI assisted clinical trial recruitment system of FIG. 1 in accordance with some embodiments of the inventive concept.

FIG. 3 is a block diagram of the AI engine 145 incorporating a machine learning system in accordance with some embodiments of the inventive concept.

As shown in FIG. 3, the AI engine module 145 may include both training modules and modules used for processing new data on which to identify patients for participation in a clinical trial. The modules used in the training portion of the AI engine module 145 include the training data 305, the featuring module 325, the labeling module 330, and the machine learning engine 340. The training data 305 may comprise information associated with historical medical record chart data as described above with respect to the medical record chart data 205 of FIG. 2. The training data 305 may also include examples of clinical trial selection criteria and/or screening requirements. The featuring module 325 is configured to identify the individual independent variables that are used by the AI engine module 145 to determine a match between characteristics of a patient's medical record data and one or more clinical trial selection criteria and/or screening requirements, which may be considered a dependent variable. For example, the training data 305 may be generally unprocessed or formatted and include extra information in addition to medical claim information and clinical trial selection criteria and/or screening requirements. For example, the medical record data may include account codes, business address information, and the like, which can be filtered out by the featuring module 325. The features extracted from the training data 305 may be called attributes and the number of features may be called the dimension. The labeling module 330 may be configured to assign defined labels to the training data and to clinical trial patient match determinations to ensure a consistent naming convention for both the input features and the generated outputs. The machine learning engine 340 may process both the featured training data 305, including the labels provided by the labeling module 330, and may be configured to test numerous functions to establish a quantitative relationship between the featured and labeled input data and the generated outputs. The machine learning engine 340 may use modeling techniques to evaluate the effects of various input data features on the generated outputs. These effects may then be used to tune and refine the quantitative relationship between the featured and labeled input data and the generated outputs. The tuned and refined quantitative relationship between the featured and labeled input data generated by the machine learning engine 240 is output for use in the AI engine 345. The machine learning engine 340 may be referred to as a machine learning algorithm.

The modules used for processing new data on which to determine whether characteristics of a patient's medical record data match one or more selection criteria and/or screening requirements for a clinical trial include the new data 355, the featuring module 365, the AI engine module 345, and the patient match module 375. The new data 355 may be the same data/information as the training data 305 in content and form except the data will be used for an actual determination of whether a patient's medical record data match the clinical trial selection criteria and/or screening requirements using a thresholding analysis as described above. Likewise, the featuring module 365 performs the same functionality on the new data 355 as the featuring module 325 performs on the training data 305. The AI engine 345 may, in effect, be generated by the machine learning engine 340 in the form of the quantitative relationship determined between the featured and labeled input data and the generated outputs. The AI engine 345 may, in some embodiments, be referred to as an AI model. The AI engine 345 may be configured to output a determination of whether a patient's medical record information matches with the clinical trial selection criteria and/or screening requirements based on a threshold analysis via the patient match module 375. The patient match module 375 may be configured to communicate the identification of the patient as a clinical trial patient candidate to the provider that serves the patient. As described above, the identity of a clinical trial patient candidate may be communicated to the provider asynchronously by transmitting a communication to the provider (e.g., an email, call, letter, or the like). In other embodiments, if the provider, for example, has an onsite trial coordinator, then the identity of the trial patient candidate may be communicated through a networked results portal for the trial that the provider has access to.

Figures 5, 6:
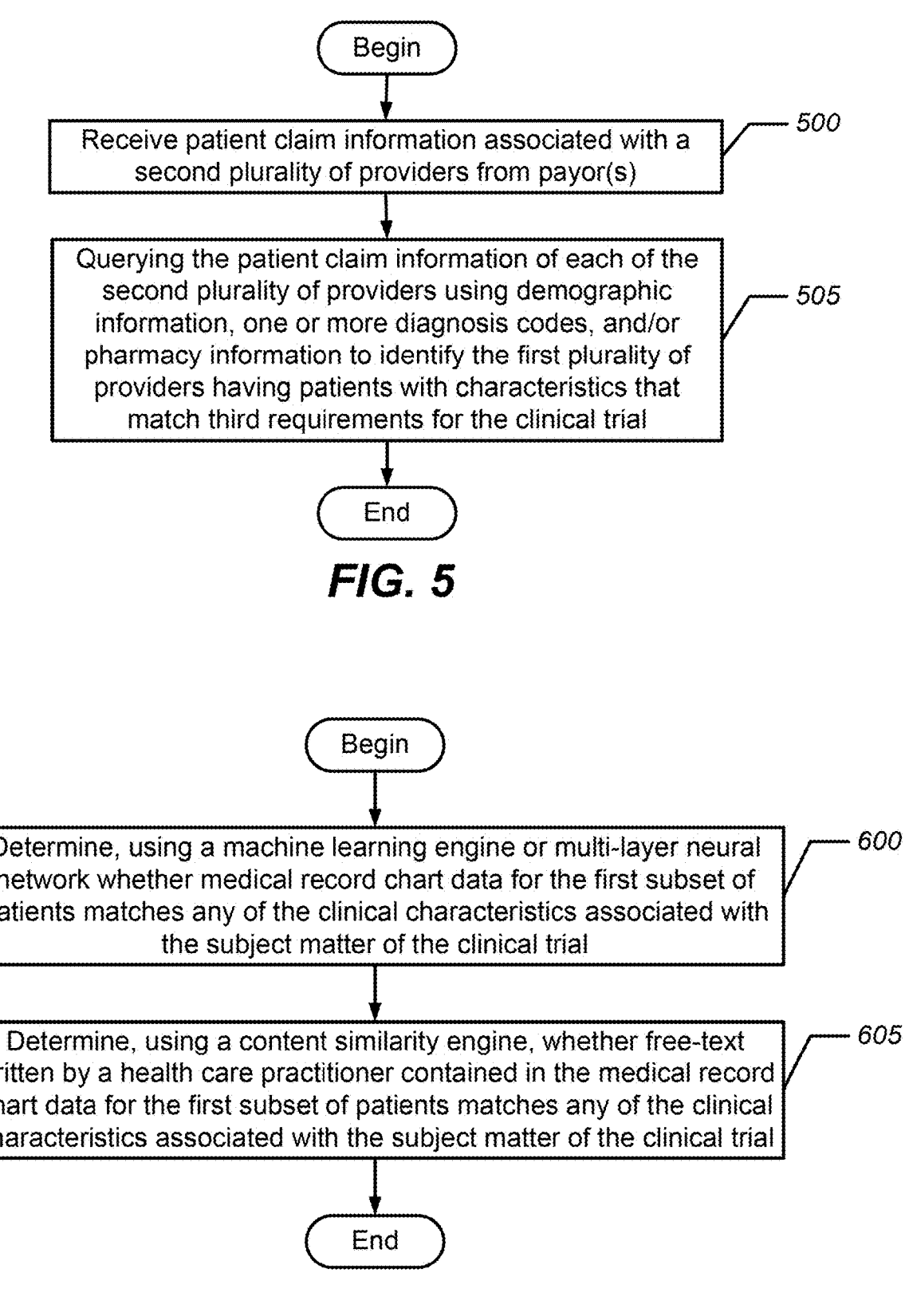

FIGS. 4-6 are flowcharts that illustrate operations for coordinated identification of patients served by multiple providers using the AI assisted clinical trial recruitment system of FIG. 1 in accordance with some embodiments of the inventive concept. Referring now to FIG. 4, operations begin at block 400 where the AI server 140 may receive patient medical record information from each of a plurality of providers. The providers may be associated with a plurality of different organizational managing entities, respectively. At block 405, the patient medical record information is queried using selection criteria to identify a first subset of patients that have characteristics that match the first screening requirements for a clinical trial. The selection criteria may include, but is not limited to, patient demographic information, one or more diagnoses codes, and/or medical history information. these selection criteria may include, but are not limited to, laboratory test values, medication names, scores for cognitive tests, medical professional observations, acute condition names, chronic condition names, and/or allergy names. The AI engine may use the neural network 210, the content similarity engine 215, and/or the machine learning system of FIG. 3 to identify ones of the first subset of patients whose medical record information includes second characteristics that match second screening requirements for the clinical trial at block 410. The first screening requirements may define individual thresholds for one or more of the selection criteria and a matching threshold for a number of the individual thresholds that must be met to be considered a match. Likewise, the second screening requirements may define individual thresholds for one or more of the second characteristics and a matching threshold for a number of the individual thresholds that must be met to be considered match. The operations of block 410 may be repeated in iterative fashion to compare ever more data from the medical record information with more detailed and granular screening requirements for the clinical trial. Once one or more clinical trial patient candidates have been identified at block 410, the identities of these patients may be communicated to their corresponding provider(s) at block 415. As described above, the identity of a clinical trial patient candidate may be communicated to the provider asynchronously by transmitting a communication to the provider (e.g., an email, call, letter, or the like). In other embodiments, if the provider, for example, has an onsite trial coordinator, then the identity of the trial patient candidate may be communicated through a networked results portal for the trial that the provider has access to. Patient data that is accessed for determining trial candidacy may be securely discarded after the process of identifying patients for a clinical trial is complete. This data may not used for other purposes or saved for identifying patients for other clinical trials to ensure compliance with medical record handling and security laws and regulations.

Referring now to FIG. 5, embodiments for identifying the plurality of providers begin at block 500 where patient claim information is received at the AI server 140 for a second larger plurality or providers. The patient claim information received from one or more payors is queried at block 505 using, for example, selection criteria based on de-identified patient information, such as demographic information, one or more diagnosis codes, and/or pharmacy information. This query of the patient claim information may identify those patients of the providers that have third characteristics that match third screening requirements for the clinical trial. The third screening requirements may define individual thresholds for one or more of the third characteristics and a matching threshold for a number of the individual thresholds that must be met to be considered a match in similar fashion to the thresholding described above with respect to the medical record information. Based on this query, the first plurality of providers may be identified from the larger second plurality of providers for which the claim information was obtained. In some embodiments, a further threshold analysis may be performed to ensure that each of the first plurality of providers provides health care services to or is otherwise associated with a number of patient candidates for the clinical trial that is greater than a defined lower bound based on the selection criteria used in the query. If an identified provider is associated with too few patient candidates for the clinical trial based on the claim information query, then the provider may be excluded from the identified first plurality of providers whose patients' medical record information is further analyzed as described above to identify patient candidates for the clinical trial. The selection criteria and/or the patient candidate threshold may be modified and the querying operation of block 505 may be repeated until a number of providers that each serve a number of patient candidates for the clinical trial that is greater than the defined lower bound are identified to increase the likelihood that a sufficient number of patients may be identified as candidates for the clinical trial. In some embodiments, providers may be geo-targeted using zip-codes or other geographic identifying indicia from the patient claim information to identify or select providers in a particular geographic area. Thus, according to some embodiments of the inventive concept, payor claim information may be reviewed and queried to determine those providers that are likely to have patients that may be good candidates for a clinical trial.

In accordance with various embodiments of the inventive concept, multiple types of AI technology may be used in the clinical trial recruitment system for coordinated identification of patients served by multiple providers. Referring now to FIG. 6, the operations of block 410 may be performed beginning at block 600 where a machine learning engine, such as that described above with respect to FIG. 3 or a multi-layer neural network, such as the neural network 210 of FIG. 2, may be used to determine whether medical record chart data for the first subset of patients (i.e., those patients that have been identified using the initial clinical trial selection criteria at block 405 of FIG. 4) matches any of the clinical characteristics associated with the subject matter of the clinical trial. At block 605, a content similarity engine, such as the content similarity engine 215 of FIG. 2 is used to determine whether free-text written by a health care practitioner contained in the medical record chart data for the first subset of patients matches any of the clinical characteristics associated with the subject matter of the clinical trial.

Figure 7:
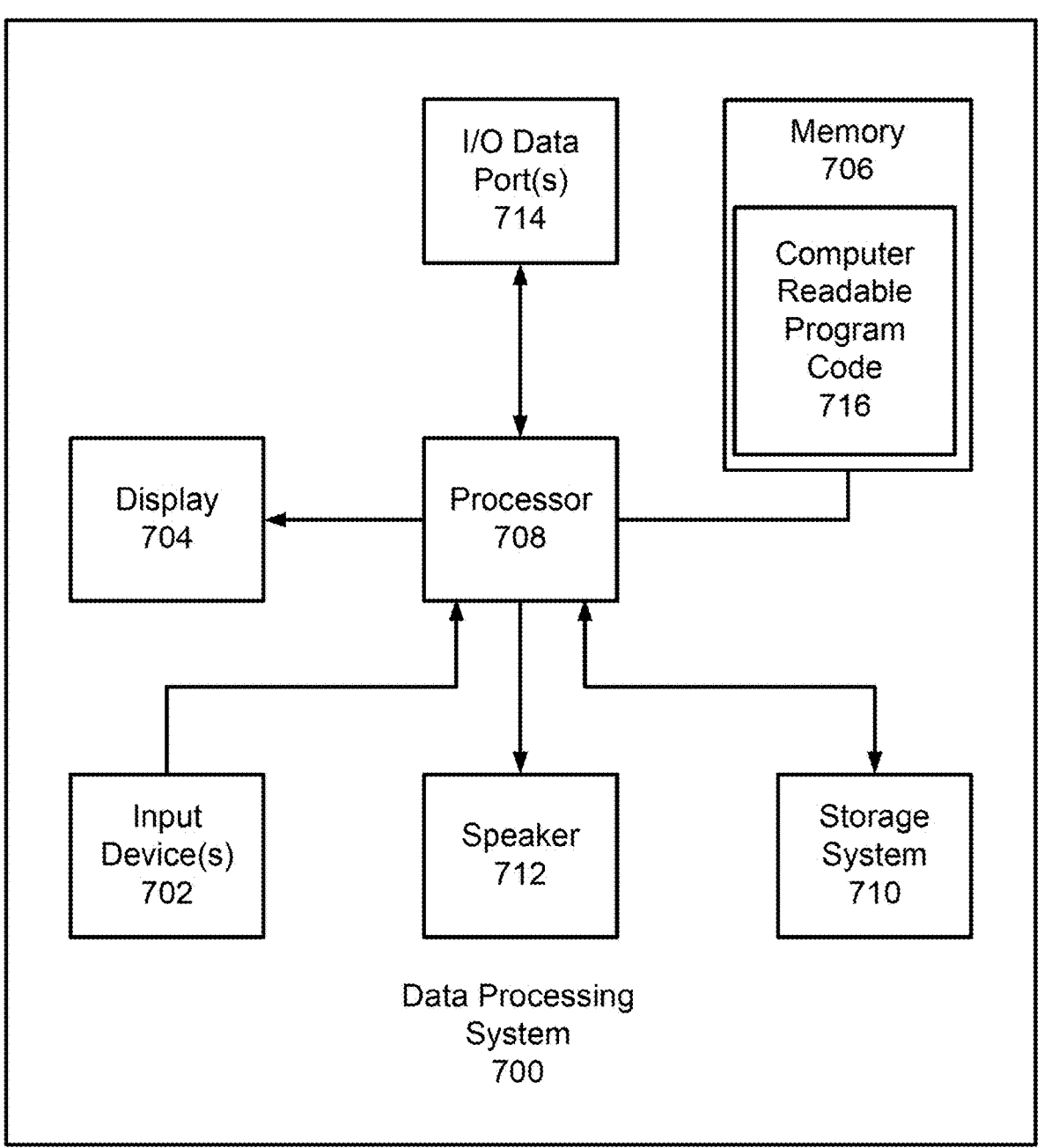
FIG. 7 is a data processing system that may be used to implement one or more servers in the AI assisted clinical trial recruitment system of FIG. 1 in accordance with some embodiments of the inventive concept.

Referring now to FIG. 7, a data processing system 700 that may be used to implement the AI server 140 of FIG. 1, in accordance with some embodiments of the inventive concept, comprises input device(s) 702, such as a keyboard or keypad, a display 704, and a memory 706 that communicate with a processor 708. The data processing system 700 may further include a storage system 710, a speaker 712, and an input/output (I/O) data port(s) 714 that also communicate with the processor 708. The processor 708 may be, for example, a commercially available or custom microprocessor. The storage system 810 may include removable and/or fixed media, such as floppy disks, ZIP drives, hard disks, or the like, as well as virtual storage, such as a RAMDISK. The I/O data port(s) 714 may be used to transfer information between the data processing system 700 and another computer system or a network (e.g., the Internet). These components may be conventional components, such as those used in many conventional computing devices, and their functionality, with respect to conventional operations, is generally known to those skilled in the art. The memory 706 may be configured with computer readable program code 716 to facilitate AI assisted clinical trial recruitment according to some embodiments of the inventive concept.

Figure 8:
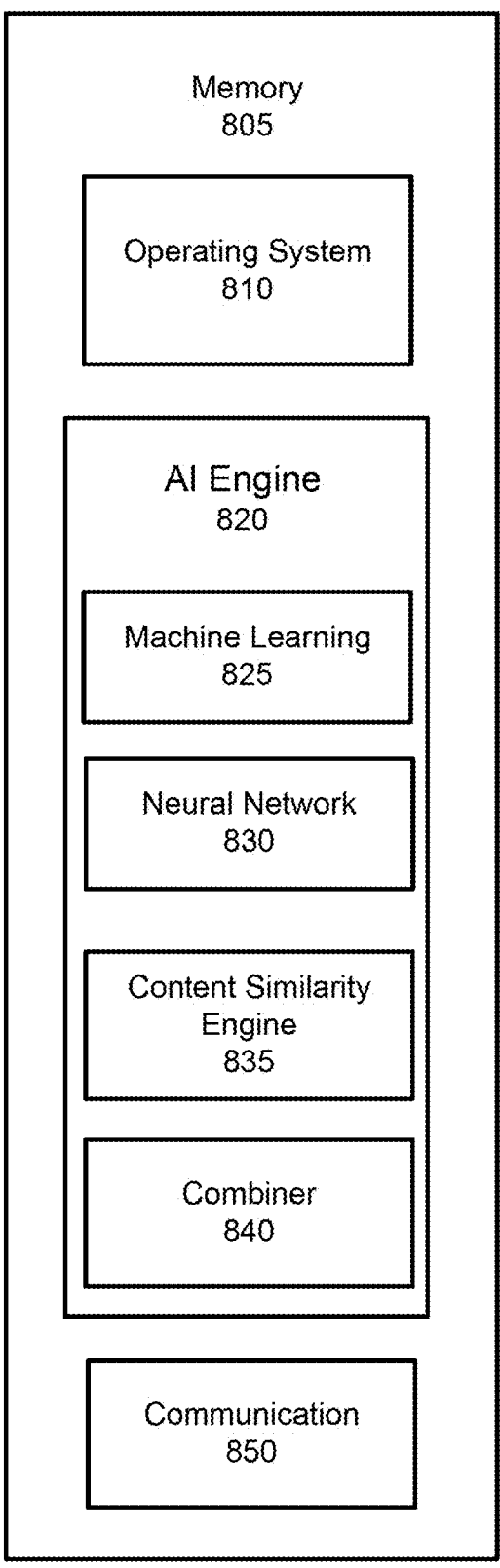
FIG. 8 is a block diagram that illustrates a software/hardware architecture for use in the AI assisted clinical trial recruitment system of FIG. 1 in accordance with some embodiments of the inventive concept.

FIG. 8 illustrates a memory 805 that may be used in embodiments of data processing systems, such as the AI server 140 of FIG. 1, the health care facility interface server 130 of FIG. 1, and the data processing system 700 of FIG. 7, respectively, to facilitate AI assisted clinical trial recruiting according to some embodiments of the inventive concept. The memory 805 is representative of the one or more memory devices containing the software and data used for facilitating operations of the AI server 140 and AI engine module 145 as described herein. The memory 805 may include, but is not limited to, the following types of devices: cache, ROM, PROM, EPROM, EEPROM, flash, SRAM, and DRAM. As shown in FIG. 8, the memory 805 may contain three or more categories of software and/or data: an operating system 810, an AI engine module 820, and a communication module 850. In particular, the operating system 810 may manage the data processing system's software and/or hardware resources and may coordinate execution of programs by the processor. The AI engine module 820 may include a machine learning module 825, a neural network module 830, a content similarity engine module 835, and a combiner module 840. The machine learning module 825 may be configured to perform one or more of the operations described above with respect to FIG. 3 and the flowcharts of FIGS. 4-6. The neural network module 830 may be configured to perform one or more of the operations described above with respect to the neural network 210 of FIG. 2 and the flowcharts of FIGS. 4-6. The content similarity engine module 835 may be configured to perform one or more of the operations described above with respect to the content similarity engine 215 of FIG. 2 and the flowcharts of FIGS. 4-6. The combiner module 840 may be configured to perform one or more of the operations described above with respect to the combiner 220 of FIG. 2 and the flowcharts of FIGS. 4-6. The communication module 850 may be configured to support communication between, for example, the AI server 140 and the health care facility interface server 130, between the health care facility interface server 130 and the health care facility servers 105*a*, 105*b*, and between the health care facility interface server 130 and the payors 160*a*, 160*b*.

Although FIGS. 7-8 illustrate hardware/software architectures that may be used in data processing systems, such as the AI server 140 of FIG. 1, the health care facility interface server 130 and the data processing system 700 of FIG. 7, respectively, in accordance with some embodiments of the inventive concept, it will be understood that embodiments of the present invention are not limited to such a configuration but is intended to encompass any configuration capable of carrying out operations described herein.

Computer program code for carrying out operations of data processing systems discussed above with respect to FIGS. 1-8 may be written in a high-level programming language, such as Python, Java, C, and/or C++, for development convenience. In addition, computer program code for carrying out operations of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Moreover, the functionality of the AI server 140 of FIG. 1, the health care facility interface server 130 of FIG. 1, and the data processing system 700 of FIG. 7 may each be implemented as a single processor system, a multi-processor system, a multi-core processor system, or even a network of stand-alone computer systems, in accordance with various embodiments of the inventive concept. Each of these processor/computer systems may be referred to as a "processor" or "data processing system."

The data processing apparatus described herein with respect to FIGS. 1-8 may be used to facilitate AI assisted clinical trial recruitment according to some embodiments of the inventive concept described herein. These apparatus may be embodied as one or more enterprise, application, personal, pervasive and/or embedded computer systems and/or apparatus that are operable to receive, transmit, process and store data using any suitable combination of software, firmware and/or hardware and that may be standalone or interconnected by any public and/or private, real and/or virtual, wired and/or wireless network including all or a portion of the global communication network known as the Internet, and may include various types of tangible, non-transitory computer readable media. In particular, the memory 805 when coupled to a processor includes computer readable program code that, when executed by the processor, causes the processor to perform operations including one or more of the operations described herein with respect to FIGS. 1-6.

Some embodiments of the inventive concept described herein may provide an AI assisted clinical trial recruitment system for coordinated identification of patients served by multiple providers, which may be associated with a plurality of different organizational managing entities, respectively. The AI assisted trial recruitment system may be used to create relationships between trial managers and providers, such that providers likely to have patients that may be good candidates for the trial may be identified through patient claims data obtained from payors and, once identified, these providers may opt in to participate in finding patients for a current trial or future trials by providing access to their patients' records. A trial manager may then use the AI assisted clinical trial recruitment system to identify patient candidates at multiple provider facilities and then reach out to the providers to share with them the identities of the patient candidates to encourage the providers to consult with the patients to inform them about their opportunity to participate in the trial. Thus, trial managers do not need to rely on social media campaigns with the hope that patients will seek out access to the trial on their own. This may improve rates of patient recruitment for clinical trials, provide additional patient consults for providers, and provide patients with additional care options.

Further Definitions and Embodiments

In the above description of various embodiments of the present inventive concept, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

The flowchart and block diagrams in the figures illustrate the architecture, functionality, and operation of possible implementations of systems, methods, and computer program products according to various aspects of the present inventive concept. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

In the above-description of various embodiments of the present inventive concept, aspects of the present inventive concept may be illustrated and described herein in any of a number of patentable classes or contexts including any new and useful process, machine, manufacture, or composition of matter, or any new and useful improvement thereof. Accordingly, aspects of the present inventive concept may be implemented entirely hardware, entirely software (including firmware, resident software, micro-code, etc.) or combining software and hardware implementation that may all generally be referred to herein as a "circuit," "module," "component," or "system." Furthermore, aspects of the present inventive concept may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

The description of the present inventive concept has been presented for purposes of illustration and description, but is not intended to be exhaustive or limited to the inventive concept in the form disclosed. Many modifications and variations will be apparent to those of ordinary skill in the art without departing from the scope and spirit of the inventive concept. The aspects of the inventive concept herein were chosen and described to best explain the principles of the inventive concept and the practical application, and to enable others of ordinary skill in the art to understand the inventive concept with various modifications as are suited to the particular use contemplated.

18

What is claimed is:

1. A computer-implemented method, comprising:

obtaining, by one or more processors, a set of medical records from a set of providers;

querying, by the one or more processors, the set of medical records obtained from the set of providers using one or more selection criteria to determine a patient of the set of patients has one or more characteristics that match one or more first predetermined clinical trial selection criteria, wherein the one or more selection criteria includes demographic information, one or more diagnosis codes, laboratory test values, medication names, scores for cognitive tests, medical professional observations, acute condition names, chronic condition names, or allergy names;

receiving, by the one or more processors, a medical record of the set of medical records that is associated with the patient, the medical record including a first subset of data and a second subset of data, the first subset of data including structured data and the second subset of data including unstructured text;

upon detecting, by the one or more processors, that the medical record includes the unstructured text:

performing, by the one or more processors and via a set of featurization layers of a neural network, feature extraction on the first subset of data to generate a first vector representation of the first subset of data to reduce the dimensionality of the first subset of data, wherein performing the feature extraction further comprises:

performing an encoding technique and an embedding technique to generate, based at least in part on the first subset of data, a categorical value information input vector and a sequence of categorical value information input vector, and concatenating the first subset of data with the categorical value information input vector and the sequence of categorical value information input vector to generate the first vector representation;

generating, by the one or more processors and via a set of classification layers of the neural network and based at least in part on the first vector representation, a first output by correlating the first vector representation of the first subset of data with second predetermined clinical trial selection criteria, the set of classification layers being trained based at least in part on the second predetermined clinical trial selection criteria;

generating, by the one or more processors and via a content similarity engine performing a natural language processing technique, a second output by comparing a second vector representation of the second subset of data with the second predetermined clinical trial selection criteria including applying a natural language processing technique to the second subset of data to generate segments containing sequences of words, weighting the words based on importance of the words with respect to a respective segment and importance of the words with respect to all of the segments using term frequency-inverse document frequency (td-idf), and performing a weighted comparison of the second vector representation of the second subset of data with the second predetermined clinical trial selection criteria;

merging, by the one or more processors, the first output and the second output into a third output;

determining, by the one or more processors, that the patient matches the second predetermined clinical trial selection criteria based on the third output satisfying a predetermined threshold;

transmitting, by the one or more processors and via a communication network, an identity of the patient to a provider of the set of providers; and discarding, by the one or more processors, the set of medical records so that the set of medical records is not used in determining patient candidacy in subsequent clinical trials.

2. The computer-implemented method of claim 1, further comprising:

identifying, by the one or more processors and using patient claim information associated with the set of providers, the provider of the set of providers having a number of patients that include one or more characteristics that satisfy provider selection criteria and that exceeds a patient number threshold;

wherein the patient is one of the number of patients of the provider of the set of providers.

3. The computer-implemented method of claim 2, wherein identifying the provider of the set of providers comprises:

querying, by the one or more processors, the patient claim information of each of the set of providers using demographic information, one or more diagnosis codes, or pharmacy information to identify ones of the set of providers having patients with the one or more characteristics that match the one or more first predetermined clinical trial selection criteria.

4. The computer-implemented method of claim 2, wherein identifying the provider of the set of providers comprises:

querying, by the one or more processors, the patient claim information of each of the set of providers using de-identified patient information to identify ones of the set of providers having patients with the one or more characteristics that match the one or more first predetermined clinical trial selection criteria.

5. The computer-implemented method of claim 1, wherein transmitting the identity of the patient comprises:

transmitting, by the one or more processors and via the communication network, the identity of the patient to the provider of the set of providers via a networked results portal accessible by the provider.

6. The computer-implemented method of claim 1, further comprising:

receiving, by the one or more processors, a communication from the provider of the set of providers opting in to participating in the clinical trial.

7. The computer-implemented method of claim 1, wherein the second predetermined clinical trial selection criteria comprise demographic information, one or more diagnosis codes, laboratory test values, medication names, scores for cognitive tests, medical professional observations, acute condition names, chronic condition names, or allergy names.

8. A system, comprising:

one or more processors; and one or more memories storing processor-executable instructions that, when executed by the one or more processors, cause the one or more processors to perform operations comprising:

obtaining a set of medical records from a set of providers;

querying the set of medical records obtained from the set of providers using one or more selection criteria to determine a patient of the set of patients has one or more characteristics that match one or more first predetermined clinical trial selection criteria, wherein the one or more selection criteria includes demographic information, one or more diagnosis codes, laboratory test values, medication names, scores for cognitive tests, medical professional observations, acute condition names, chronic condition names, or allergy names;

receiving a medical record of the set of medical records that is associated with the patient, the medical record including a first subset of data and a second subset of data, the first subset of data including structured data and the second subset of data including unstructured text;

upon detecting that the medical record includes the unstructured text:

performing, via a set of featurization layers of a neural network, feature extraction on the first subset of data to generate a first vector representation of the first subset of data to reduce the dimensionality of the first subset of data wherein performing the feature extraction further comprises:

performing an encoding technique and an embedding technique to generate, based at least in part on the first subset of data, a categorical value information input vector and a sequence of categorical value information input vector, and concatenating the first subset of data with the categorical value information input vector and the sequence of categorical value information input vector to generate the first vector representation;

generating, via a set of classification layers of the neural network and based at least in part on the first vector representation, a first output by correlating the first vector representation of the first subset of data with second predetermined clinical trial selection criteria, the set of classification layers being trained based at least in part on the second predetermined clinical trial selection criteria;

generating, via a content similarity engine performing a natural language processing technique, a second output by comparing a second vector representation of the second subset of data with the second predetermined clinical trial selection criteria including applying a natural language processing technique to the second subset of data to generate segments containing sequences of words, weighting the words based on importance of the words with respect to a respective segment and importance of the words with respect to all of the segments using term frequency-inverse document frequency (td-idf), and performing a weighted comparison of the second vector representation of the second subset of data with the second predetermined clinical trial selection criteria;

merging the first output and the second output into a third output;

determining that the patient matches the second predetermined clinical trial selection criteria based on the third output satisfying a predetermined threshold; and transmitting via a communication network, an identity of the patient to a provider of the set of providers; and discarding the set of medical records so that the set of medical records is not used in determining patient candidacy in subsequent clinical trials.

9. The system of claim 8, wherein receiving the medical record associated with the patient comprises:

determining that the medical record associated with the patient includes one or more characteristics that satisfy one or more selection criterion.

10. The system of claim 8, wherein the operations further comprise:

identifying, using patient claim information associated with the set of providers, the provider of the set of providers having a number of patients that include one or more characteristics that satisfy provider selection criteria and that exceeds a patient number threshold;

wherein the patient is one of the number of patients of the provider of the set of providers.

11. The system of claim 10, wherein identifying the provider of the set of providers comprises:

querying the patient claim information of each of the set of providers using demographic information, one or more diagnosis codes, or pharmacy information to identify ones of the set of providers having patients with the one or more characteristics that match the one or more first predetermined clinical trial selection criteria.

12. The system of claim 8, wherein transmitting the identity of the patient comprises:

transmitting, via the communication network, the identity of the patient to the provider of the set of providers via a networked results portal accessible by the provider.

13. One or more non-transitory computer-readable media storing processor-executable instructions that, when executed by one or more processors, cause the one or more processors to perform operations comprising:

obtaining a set of medical records from a set of providers;

querying the set of medical records obtained from the set of providers using one or more selection criteria to determine a patient of the set of patients has one or more characteristics that match one or more first predetermined clinical trial selection criteria, wherein the one or more selection criteria includes demographic information, one or more diagnosis codes, laboratory test values, medication names, scores for cognitive tests, medical professional observations, acute condition names, chronic condition names, or allergy names;

receiving a medical record of the set of medical records that is associated with the patient, the medical record including a first subset of data and a second subset of data, the first subset of data including structured data and the second subset of data including unstructured text;

upon detecting that the medical record includes the unstructured text:

performing, via a set of featurization layers of a neural network, feature extraction on the first subset of data to generate a first vector representation of the first subset of data to reduce the dimensionality of the first subset of data, wherein performing the feature extraction further comprises:

performing an encoding technique and an embedding technique to generate, based at least in part on the first subset of data, a categorical value information input vector and a sequence of categorical value information input vector, and concatenating the first subset of data with the categorical value information input vector and the sequence of categorical value information input vector to generate the first vector representation;

generating, via a set of classification layers of the neural network and based at least in part on the first vector representation, a first output by correlating the first vector representation of the first subset of data with second predetermined clinical trial selection criteria, the set of classification layers being trained based at least in part on the second predetermined clinical trial selection criteria;

generating, via a content similarity engine performing a natural language processing technique, a second output by comparing a second vector representation of the second subset of data with the second predetermined clinical trial selection criteria including applying a natural language processing technique to the second subset of data to generate segments containing sequences of words, weighting the words based on importance of the words with respect to a respective segment and importance of the words with respect to all of the segments using term frequency-inverse document frequency (td-idf), and performing a weighted comparison of the second vector representation of the second subset of data with the second predetermined clinical trial selection criteria;

merging the first output and the second output into a third output;

determining that the patient matches the second predetermined clinical trial selection criteria based on the third output satisfying a predetermined threshold;

transmitting via a communication network, an identity of the patient to a provider of the set of providers; and discarding the set of medical records so that the set of medical records is not used in determining patient candidacy in subsequent clinical trials.

<div align="center">*   *   *   *   *</div>